US007230432B2

United States Patent
Cole et al.

(10) Patent No.: US 7,230,432 B2
(45) Date of Patent: Jun. 12, 2007

(54) NANOTUBE SENSOR

(75) Inventors: Barrett E. Cole, Bloomington, MN (US); Robert E. Higashi, Shorewood, MN (US)

(73) Assignee: Honeywell International Inc., Morristown, NJ (US)

(*) Notice: Subject to any disclaimer, the term of this patent is extended or adjusted under 35 U.S.C. 154(b) by 0 days.

(21) Appl. No.: 11/151,902

(22) Filed: Jun. 14, 2005

(65) Prior Publication Data

US 2005/0255032 A1 Nov. 17, 2005

Related U.S. Application Data

(62) Division of application No. 10/304,351, filed on Nov. 26, 2002, now Pat. No. 6,949,931.

(51) Int. Cl.
*G01N 27/62* (2006.01)

(52) U.S. Cl. .................. 324/464; 324/465; 427/58

(58) Field of Classification Search ........ 324/459–470, 324/715; 333/186, 197; 427/58, 402, 249.1; 205/687; 73/19.01–19.12
See application file for complete search history.

(56) References Cited

U.S. PATENT DOCUMENTS

| 6,445,006 | B1 | 9/2002 | Brandes et al. | 257/76 |
| 6,528,020 | B1* | 3/2003 | Dai et al. | 422/98 |
| 6,803,840 | B2* | 10/2004 | Hunt et al. | 333/186 |
| 6,919,730 | B2* | 7/2005 | Cole et al. | 324/715 |
| 2002/0167374 | A1 | 11/2002 | Hunt et al. | 333/186 |
| 2003/0068432 | A1 | 4/2003 | Dai et al. | 427/58 |
| 2003/0173985 | A1 | 9/2003 | Cole et al. | 324/715 |
| 2003/0218224 | A1* | 11/2003 | Schlaf et al. | 257/414 |
| 2004/0043527 | A1 | 3/2004 | Bradley et al. | 438/48 |

FOREIGN PATENT DOCUMENTS

| DE | 10118200 | 10/2002 |
| KR | 2002003464 | 2/2002 |
| WO | WO 01/44796 | 6/2001 |
| WO | WO 02/092505 | 11/2002 |
| WO | WO 03/085368 | 10/2003 |

OTHER PUBLICATIONS

Collins, et al., "Extreme Oxygen Sensitivity of Electronic Properties of Carbon Nanotubes," Science, vol. 287, pp. 1801-1804, Mar. 10, 2000.

(Continued)

*Primary Examiner*—Minh Chau
(74) *Attorney, Agent, or Firm*—Kris T. Fredrick

(57) ABSTRACT

A sensor having a nanotube grown on and supported by thermal bimorph structures. The nanotube rests on a heat sink during sensing gas or a liquid and is moved from the heat sink when the nanotube is heated to desorb gas or liquid from it. The heatsink may function as a gate along with the bimorph structures as the other terminals of a transistor. Current-voltage and current-gate voltage characteristics may be obtained of the nanotube as a device like a transistor. These characteristics may provide information on a gas or liquid absorbed by the nanotube.

16 Claims, 6 Drawing Sheets

OTHER PUBLICATIONS

Dai, et al., "Electric-filled-directed growth of aligned single-walled carbon nanotubes," Applied Physics Letters, vol. 79, Issue, 19, pp. 3155-3157, Nov. 5, 2001.

International Search Report from Corresponding International App. No. PCT/US03/38146. ++This report appears to use the same KR reference twice to indicate its "X" relevancy to claims 1-12, 51.

Kong, et al., "Nanotube Molecular Wires as Chemical Sensors," Science, vol. 287, pp 622-625, Jan. 28, 2000.

Lee, et al., "Hydrogen adsorption and storage in carbon nanotubes," Synthetic Metals, vol. 113, pp. 209-216, 2000.

Soh, et al., "Integrated nanotube circuits: Controlled growth and ohmic contacting of single-walled carbon nanotubes," Applied Physics Letters, vol. 75, No. 5, pp. 627-629, Aug. 2, 1999.

* cited by examiner ized to respond to certain gases. Examples are oxygen for palladium, hydrogen for platinum. Other functionalizing materials may be used with the nanotubes.

NANOTUBE SENSOR

This application is a Divisional of U.S. patent application Ser. No. 10/304,351, filed on Nov. 26, 2002 U.S. Pat. No. 6,949,931 and entitled, "Nanotube Sensor."

BACKGROUND

The invention pertains to gas sensors. Particularly, it pertains to nanotube sensors.

Certain attempts have been made to use nanotube for gas sensing. U.S. patent application Ser. No. 10/100,440, filed Mar. 18, 2002 and entitled, "Carbon Nanotube Sensor," is hereby incorporated by reference.

SUMMARY

Nanotubes can be grown in-situ in a directed manner in a certain gas environment by bridging a moat between two moveable finger- or arm-like support pieces, connections or electrodes for the nanotubes. A manufacturable MEMS-base nanotube sensor can be made.

BRIEF DESCRIPTION OF THE DRAWINGS

FIGS. 7a and 7b are cross-section views of a nanotube sensor similar to that in FIG. 6a.

DESCRIPTION

Figure 1A:
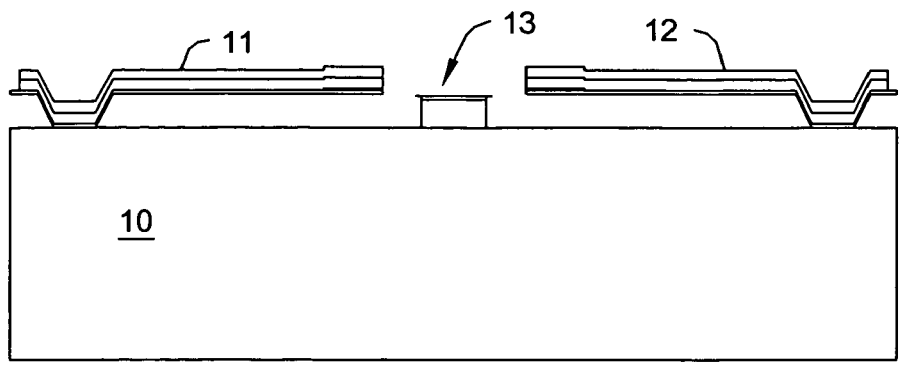
FIGS. 1a and 1b show a sensor structure that supports a nanotube.

FIG. 1a shows a basic structure that supports a nanotube. Bimorph finger- or arm-like longitudinal structures 11 and 12 are situated on substrate 10. A pedestal-like structure 13 may be situated between the ends of structures 11 and 12 on substrate 10. Structure 13 may be utilized as a heat sink or an electrode or both.

Figure 1B:
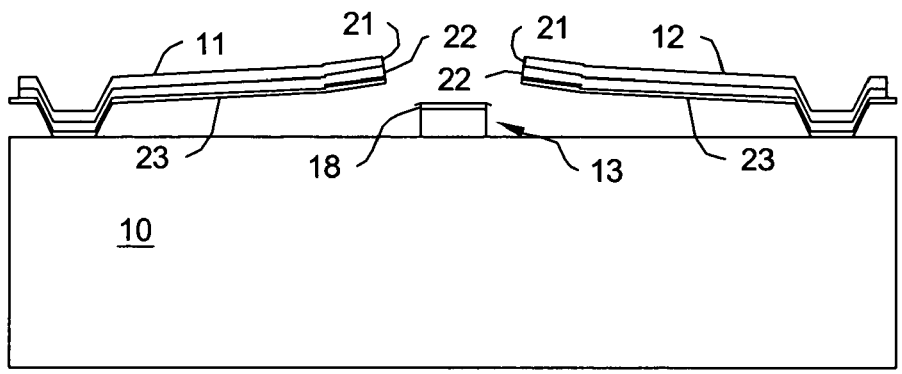

Structures 11 and 12 may be composed of a top metal layer 21 and a bottom 22 dielectric, or vice versa. These structures may have other compositions. In FIG. 1b, structures 11 and 12 may be heated and their ends will move away from structure 13 and substrate 10 due to the heat.

Figure 2A:
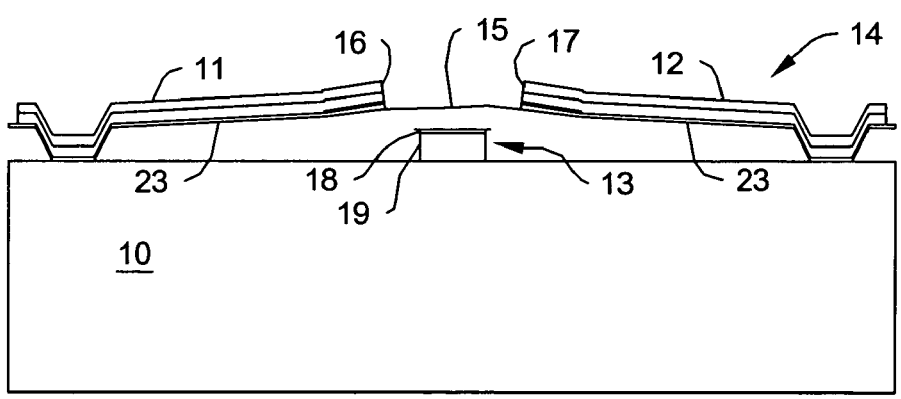
FIGS. 2a and 2b show a sensor structure that has a nanotube.
Figure 2B:
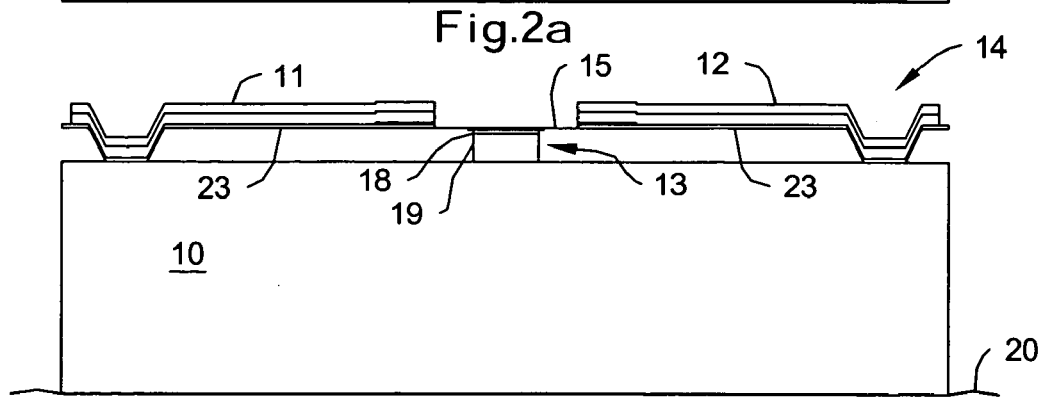

In FIG. 2a, while fingers or arms 11 and 12 are raised up, one or more nanotubes may be grown bridging the two closer ends of structures 11 and 12. This growing may be performed in an atmosphere or local environment of ethylene, methane, CO or the like. A nanotube or nanotubes are grown upon heating the structures to between approximately 700 and 900 degrees Celsius. Generally, one may result in having a carbon single-walled (i.e., one layer of molecules) nanotube 15 bridging the ends facing each other of structure 11 and 12. The nanotube may grow by virtue of flow and/or an electric field from one end to the other of structures 11 and 12. When device 14 is removed from the heat of a furnace or other heat source, structures 11 and 12 cool and their ends 16 and 17 move towards substrate 10 as shown in FIG. 2b. This activity causes nanotube 15 to sit on heat sink/electrode 13. Structure 13 may be composed of a metal 19 that has been coated with a thin passivation layer 18. Device 14 can be cut out as a die and mounted on a header for operation.

When nanotube 15 has cooled down, it may be exposed to a fluid and absorb some of it. A fluid may be a gas or a liquid. "Gas" is to be referred to in this description but may be interchanged with "liquid". When device 14 is heated as a die, nanotube 14 is lifted off of post or pedestal 13 by structures 11 and 12 when the latter bend as a result of their bimorph structures being heated. When nanotube 15 is heated, absorbed gases are driven off nanotube 15, making it ready for resorption of new gases. When the heat is removed, arms 11 and 12 come down; nanotube 15 sits on heat sink 13 which removes heat from nanotube 15. Then nanotube 15 is ready for resorption of new gas in the sensor's immediate environment.

To lift nanotube 15 off of heat sink 13, arms 11 and 12 may be actuated several different ways. Device 14 as a die on a header 20 may be heated or structure 11 and 12 may have heating elements in them. In either case, nanotube 15 is removed from contact with heat sink 13 so that nanotube 15 can more rapidly heat up and desorb any gas on it, as shown in FIG. 2a. After this, heat is removed from header 20 or heating elements 23 in arms 11 and 12 are disconnected. Structures 11 and 12 move towards substrate 10 and nanotube 15 rests on heat sink 13 to further cool off and be ready for absorption of a new gas.

Figure 3A:
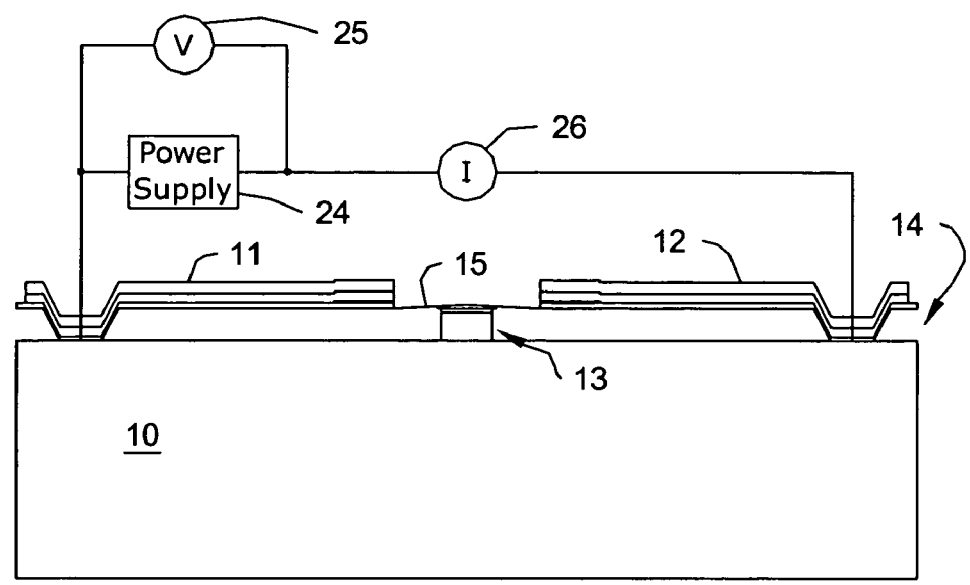
FIGS. 3a and 3b show electrical configurations of a nanotube sensor.

FIG. 3a shows an electrical configuration which may be used to aid in identifying a gas absorbed by nanotube 15. Power supply 24 is connected to structure 11 and 12 which become connections to nanotube 15. The current indication from meter 26 and the voltage indication from meter 25 may be noted, and from such IV characteristics, information about or identification of a gas or liquid absorbed by nanotube 15 may be obtained.

Figure 3B:
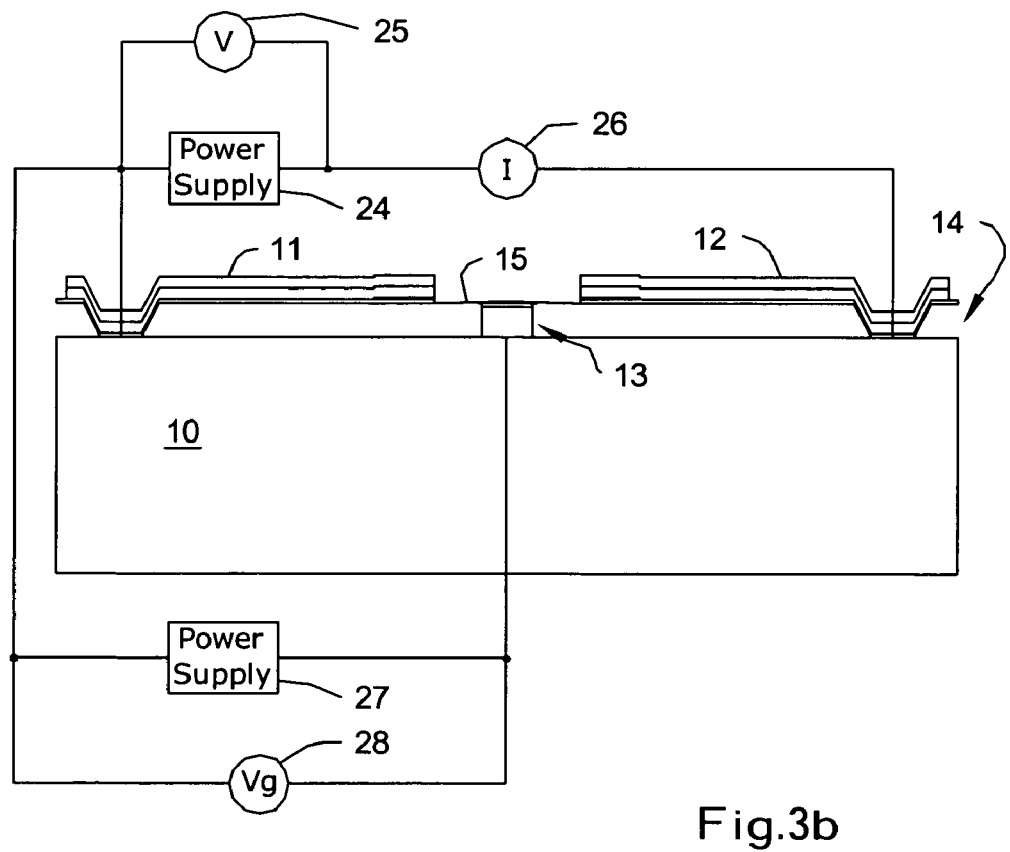

FIG. 3b shows a three terminal electrical configuration resembling a field effect transistor having a power supply 27 and a meter 28 for measuring gate-voltage. Structure 13 is the gate and structures 11 and 12 are the source and drain, respectively. The other electrical aspects of this figure are similar to those shown in FIG. 3a. The current (I) meter 26 and the gate voltage ($V_g$) meter 28 may be noted, and from such $IV_g$ characteristics, information about or identification of a gas or a liquid absorbed by nanotube 15 may be obtained. On the other hand, for a predetermined $V_g$ set by power supply 27, the current from meter 26 and the voltage from meter 25 may be noted, and from such IV characteristics, information about or identification of a gas or liquid absorbed by nanotube 15 may be obtained. The above readings may be taken periodically over a period of time from the moment that a gas begins to be absorbed by nanotube 15. Such IV and $IV_g$ characteristics may provide additional information, such as concentrations of the gas or liquid in the environment of nanotube 15.

Figure 4:
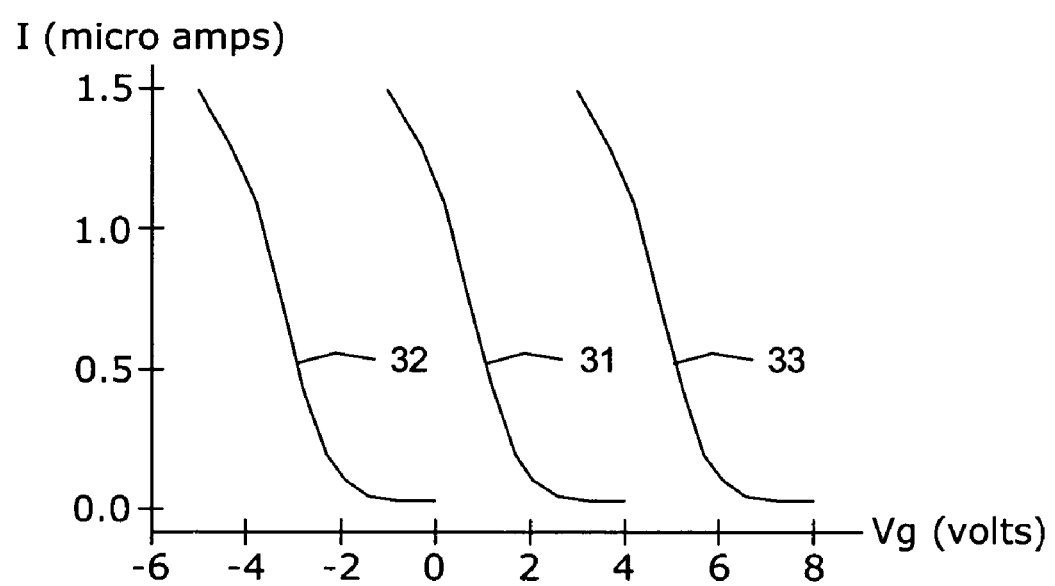
FIG. 4 is a graph of current-gate voltage curves of several gases absorbed by a nanotube of a sensor.

FIG. 4 is an example of $IV_g$ characteristics for several gases absorbed by device 14 in FIG. 3b. Curve 31 shows the $IV_g$ characteristics before gas absorption by nanotube 15. Curve 32 shows that $IV_g$ characteristics after absorption of $NH_3$ by nanotube 15. Curve 33 shows the $IV_g$ characteristics after absorption of $NO_2$ by nanotube 15. Absorption of each gas would occur after any gas or liquid in nanotube 15 was desorbed or removed. The nanotubes could be functionalized with different materials (metals, organics, semiconductors) to enhance response and discrimination for different gases.

Figure 5:
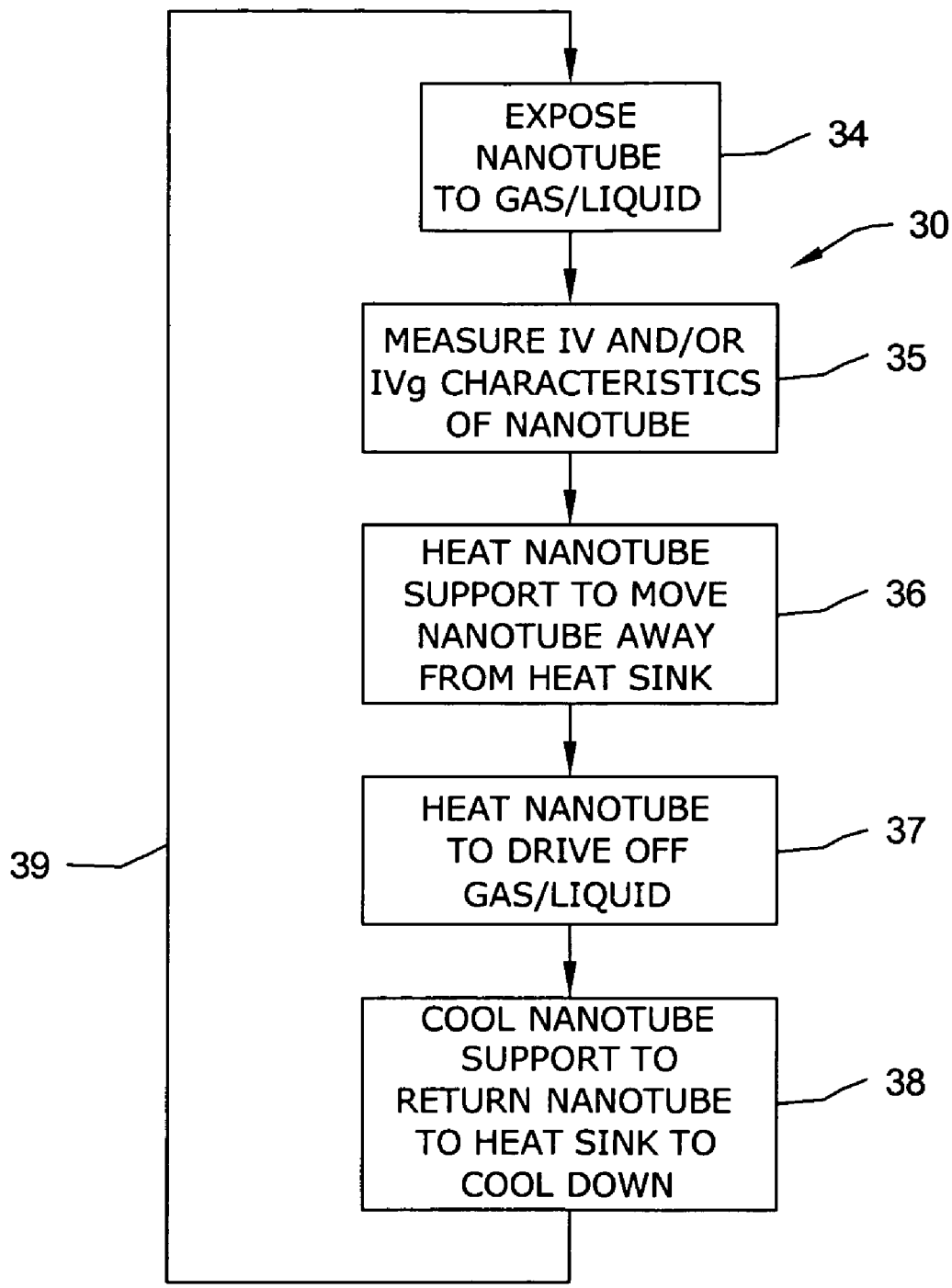
FIG. 5 is a flow diagram of a process of a nanotube sensor.

FIG. 5 shows a flow diagram 30 outlining the gas/liquid sensing process of device 14 as described above. Block 34 is exposure of nanotube 15 to the gas and/or liquid. Measuring the IV and/or the $IV_g$ characteristics of nanotube 15 is represented by block 35. Next, in block 36, nanotube 15 is moved away from heat sink 13 by support structures 11 and 12 with heat.

Heat is also used to drive off gas/liquid from nanotube 15, as represented by block 37. In block 38, structures 11 and 12 are cooled and return nanotube 15 to rest on heat sink 13 to further cool. Path 39 shows that the sensing process may repeat for sensing another or the same gas or liquid.

Figure 6A:
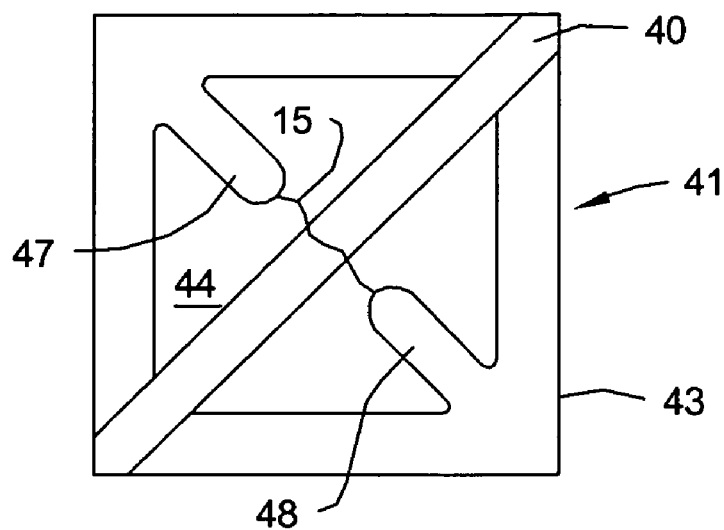
FIGS. 6a and 6b show a nanotube sensor having a cross-bar like structure.
Figure 7A:
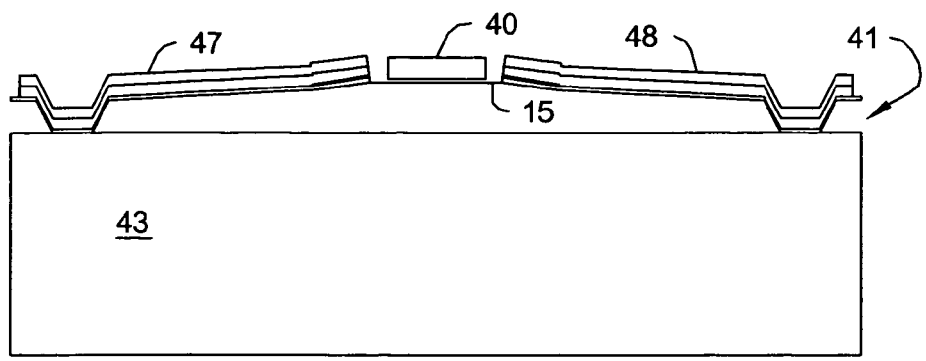
Figure 7B:
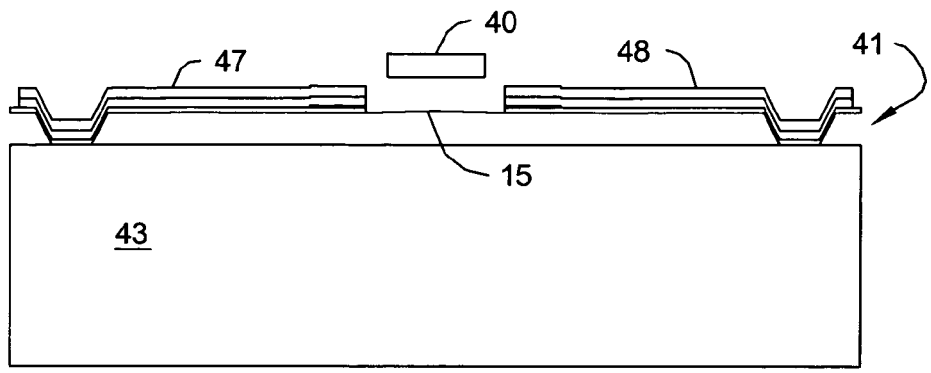

FIG. 6a reveals a plan view of a sensor 41 having a structure or crossbar 40 that may be a heat sink and/or an electrode of a transistor for purposes of attaining $IV_g$ characteristics of nanotube 15, particularly for gas/liquid sensing. Structures 47 and 48 may be the other connections to the transistor, i.e., nanotube 15. FIGS. 7a and 7b show a cross-section view of device 41. Nanotube 15 is situated between crossbar 40 and substrate 43. Structures 47 and 48 may have heating elements to heat them and nanotube 15, or substrate 43 may be heated for a similar effect. Upon heating, structures 47 and 48 lower nanotube 15 off of heatsink 40. Upon cooling, nanotube 15 is brought up to heatsink 40 and nanotube 15 is further cooled by structure 40. There may be an inverted pyramid-shaped pit 44 etched in substrate 43, for cooling or other reasons. Some other aspects of device 41 for gas/liquid sensing are like that of device 14.

Figure 6B:
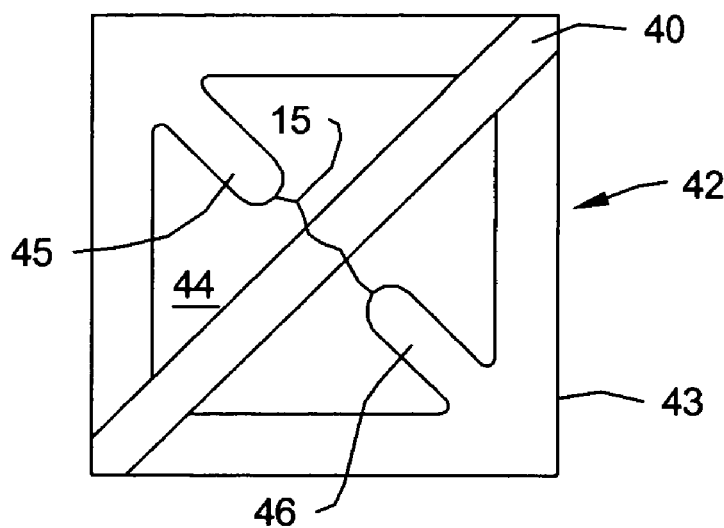
Figure 8A:
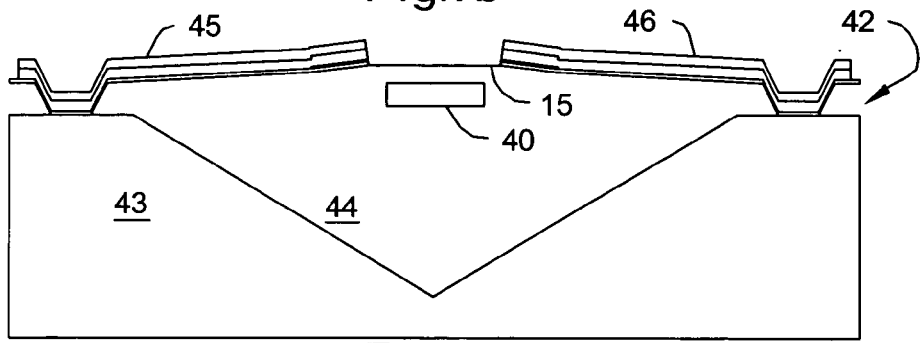
FIGS. 8a and 8b are cross-section views of a nanotube sensor similar to that in FIG. 6b.
Figure 8B:
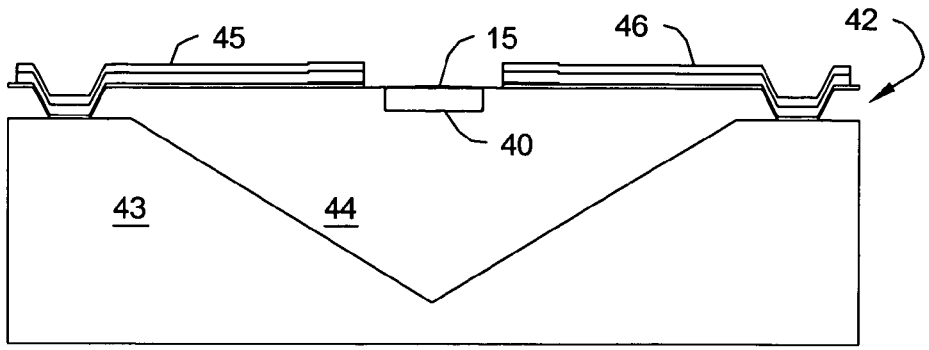

FIG. 6b shows a device 42 which has a crossbar, heatsink or gate-like structure 40 situated between nanotube 15 and substrate 43. Along with structure 40, structures 45 and 46 which are connected to nanotube 15, and with configurations like those of device 14 in FIGS. 3a and 3b, one may get IV and $IV_g$ data of nanotube 15 with or without an absorbed gas or liquid. FIGS. 8a and 8b show a cross-section of device 42. Finger- or arm-like longitudinal structures 45 and 46 that hold nanotube 15 are like that of structures 47 and 48 of device 41 except that they move away from substrate 43 rather than towards it, when heated. When structures 47 and 48 cool down, they move towards substrate 43 and nanotube 15 may be set on heatsink structure 40 for further cooling. There may be a pyramid-shaped pit 44 in substrate 43 to possibly improve cooling or facilitate other reasons for device 42. Or there may not be a pit 44. Many aspects of device 42 are like those of devices 14 and 41 for gas/liquid sensing.

Longitudinal structures 45, 46, 47 and 48 may be etched, at least in part, from substrate 43, or be formed on substrate 43. Structure 40 may be made in a similar fashion like that of structures 45, 46, 47 and 48. The structures of devices 14, 41 and 42 may be MEMS technology or be compatible with it. The technology of these devices may be silicon based or of another material.

Although the invention has been described with respect to at least one specific embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A method for sensing a gas/liquid, comprising:
   obtaining a structure having first and second terminals connected to the ends of a nanotube, respectively;
   exposing the nanotube to a gas/liquid;
   measuring a current-voltage characteristic of the nanotube;
   reviewing the current-voltage characteristic to obtain possible information about the gas/liquid; and
   heating the nanotube to desorb the gas/liquid from the nanotube.

2. The method of claim 1, further comprising:
   removing heat from the nanotube to prepare the nanotube to absorb gas/liquid.

3. A method for sensing a gas or liquid, comprising:
   obtaining a structure having source and drain terminals connected to a nanotube, and a gate terminal proximate to the nanotube;
   exposing the nanotube to a gas or liquid;
   measuring a current-gate voltage characteristic of the nanotube;
   reviewing the current-gate voltage characteristic to obtain possible information about the gas or liquid; and
   heating the nanotube to desorb the gas or liquid from the nanotube.

4. The method of claim 3, further comprising:
   removing heat from the nanotube to prepare the nanotube to absorb gas or liquid.

5. A method for sensing a fluid, comprising:
   providing a first longitudinal projection;
   providing a second longitudinal projection;
   growing at least one nanotube that connects the first and second projections;
   exposing the at least one nanotube to a fluid;
   obtaining current-voltage characteristics of the at least one nanotube, which may reveal information about the fluid; and
   heating the at least one nanotube to remove a significant portion of the fluid from the nanotube.

6. The method of claim 5, further comprising cooling the nanotube.

7. The method of claim 6, further comprising:
   exposing the at least one nanotube to another fluid;
   obtaining current-voltage characteristics of the at least one nanotube; and
   analyzing the current-voltage characteristics to obtain information about the other fluid.

8. A method for sensing a fluid comprising:
   providing a first structure;
   providing a second structure having a first end attached to the first structure, and having a second end;
   providing a third structure having a first end and attached to the first structure, and having a second end;
   providing a fourth structure on the first structure;
   connecting a nanotube across the second ends of the second and third structures, respectively;
   exposing the nanotube to a fluid; and
   measuring the current-voltage characteristics across the second and third structures; and
   wherein the second structure and the third structure are a source and a drain, respectively, of a transistor; wherein a change of temperature of the second and third structures causes the nanotube to move away from or toward the fourth structure.

9. The method of claim 8, further comprising analyzing the current-voltage characteristics to obtain information about the fluid.

10. The method of claim 8, wherein the second, third and fourth structures are a source, a drain and a gate of a transistor, respectively.

11. The method of claim 10, further comprising measuring current gate voltage ($IV_g$) characteristics of the transistor.

12. The method of claim 11, further comprising analyzing the $IV_g$ characteristics to obtain information about the fluid.

13. The method of claim 12, wherein the nanotube is a single wall of carbon molecules.

14. The method of claim 8, further comprising:
heating the second and third structures to move the nanotube away from the fourth structure; and
cooling the second and third structures to move the nanotube closer to the fourth structure.

15. The method of claim 14, wherein the fourth structure is a heat sink for the nanotube.

16. The method of claim 15, wherein:
heating the nanotube is for removing a significant portion of the fluid to which the nanotube was exposed; and
cooling the nanotube for readsorption of a fluid.

* * * * *